United States Patent
Zhang et al.

(10) Patent No.: US 12,329,795 B2
(45) Date of Patent: Jun. 17, 2025

(54) COMPOSITION FOR WEIGHT REDUCTION AND BODY FAT REDUCTION, PREPARATION METHOD AND APPLICATION THEREOF

(71) Applicants: Beijing Hengmei Jinye Nutrition and Health Technology Co., Ltd., Beijing (CN); Zhejiang Hengmei Health Technology Co., Ltd., Hangzhou (CN)

(72) Inventors: Fei Zhang, Beijing (CN); Huiru Shi, Beijing (CN); Yadan Zheng, Beijing (CN)

(73) Assignees: Beijing Hengmei Jinye Nutrition and Health Technology Co., Ltd., Beijing (CN); Zhejiang Hengmei Health Technology Co., Ltd., Hangzhou (CN)

( * ) Notice: Subject to any disclaimer, the term of this patent is extended or adjusted under 35 U.S.C. 154(b) by 0 days.

(21) Appl. No.: 18/894,385

(22) Filed: Sep. 24, 2024

(65) Prior Publication Data
US 2025/0009826 A1    Jan. 9, 2025

(30) Foreign Application Priority Data
Mar. 28, 2024  (CN) ......................... 202410361737.X

(51) Int. Cl.
| | | |
|---|---|---|
| *A61K 36/71* | (2006.01) | |
| *A61K 31/12* | (2006.01) | |
| *A61K 31/23* | (2006.01) | |
| *A61K 35/20* | (2006.01) | |
| *A61K 36/07* | (2006.01) | |
| *A61K 36/185* | (2006.01) | |
| *A61K 36/22* | (2006.01) | |
| *A61K 36/33* | (2006.01) | |
| *A61K 36/752* | (2006.01) | |
| *A61K 36/77* | (2006.01) | |
| *A61K 36/9068* | (2006.01) | |
| *A61K 38/16* | (2006.01) | |
| *A61K 38/39* | (2006.01) | |
| *A61P 3/04* | (2006.01) | |

(52) U.S. Cl.
CPC ............ *A61K 36/071* (2024.05); *A61K 31/12* (2013.01); *A61K 31/23* (2013.01); *A61K 35/20* (2013.01); *A61K 36/07* (2013.01); *A61K 36/22* (2013.01); *A61K 36/33* (2013.01); *A61K 36/577* (2024.05); *A61K 36/752* (2013.01); *A61K 36/77* (2013.01); *A61K 36/9068* (2013.01); *A61K 38/168* (2013.01); *A61K 38/39* (2013.01); *A61P 3/04* (2018.01); *A61K 2236/51* (2013.01)

(58) Field of Classification Search
None
See application file for complete search history.

(56) References Cited

U.S. PATENT DOCUMENTS

| | | |
|---|---|---|
| 2007/0026091 A1 | 2/2007 | Wang et al. |
| 2018/0333388 A1 | 11/2018 | Ling |
| 2021/0251157 A1* | 8/2021 | Leo .......................... B01D 3/12 |
| 2023/0190674 A1 | 6/2023 | Ling |

OTHER PUBLICATIONS

CNIPA, Notification of First Office Action for Chinese application CN202410361737.X, May 9, 2024.
CNIPA, Notification to grant patent right for Chinese application CN202410361737.X, Jun. 3, 2024.

* cited by examiner

*Primary Examiner* — Susan Hoffman
(74) *Attorney, Agent, or Firm* — Hemisphere Law, PLLC; Zhigang Ma

(57) ABSTRACT

A composition for weight reduction and body fat reduction, its preparation method and application are disclosed, which relates to the technical field of health food. The composition includes the following components: 10-30 parts of concentrated milk protein, 10-30 parts of soybean isolated protein powder, 10-30 parts of concentrated whey protein powder, 5-15 parts of skim milk powder, 0.5-15 parts of collagen peptide, 0.1-3 parts of *Agaricus bisporus* extract, 0.1-3 parts of *Flammulina velutipes* extract, 0.1-5 parts of okra powder, 0.1-2 parts of *Opuntia ficus-indica* extract, 1-10 parts of medium chain triglyceride microcapsule powder, 0.1-5 parts of mango concentrated powder, 0.1-2 parts of ginger oil microcapsule powder, 0.1-2 parts of citrus powder, 0.1-5 parts of guarana extract and 0.5-2 parts of compound vitamin.

8 Claims, No Drawings

COMPOSITION FOR WEIGHT REDUCTION AND BODY FAT REDUCTION, PREPARATION METHOD AND APPLICATION THEREOF

TECHNICAL FIELD

The disclosure relates to the technical field of health food, in particular to a composition for weight reduction and body fat reduction, a preparation method and application thereof.

BACKGROUND ART

Obesity has been defined by the World Health Organization as a chronic recurrent disease. The heavier the body weight, the greater the heart load, so obese people will have a higher probability of suffering from heart disease than normal people. Excessive weight can cause excessive weight on bones of the body, and cause abrasion or tearing of joints (such as vertebrae, shoulder, elbow, arm and foot joints), resulting in pain, swelling and inflammation. In addition, obesity is a major risk factor for chronic non-infectious diseases such as NIDDM, cardiovascular diseases and some cancers.

With the deepening of research, many people who are trying to lose weight have realized that dietary regulation, appropriate aerobic exercise and regular life are more conducive to increasing energy consumption and metabolic consumption of fat. Clinical studies have also shown that scientific and reasonable nutritional therapy combined exercise intervention is still the most effective and safer basic therapy at present.

Health food is also known as functional food. It is a specific type of food that does not aim at treating diseases. It has a special effect on regulating body functions, such as enhancing the body defense, preventing diseases and promoting health. It is suitable for specific groups of people to eat.

Korean patent application KR1020190137950 discloses a powdered preparation food composition for weight control, which includes apple dietary fiber powder, mixed grain powder, baked brown rice powder, crystalline fructose, chestnut powder, skim milk, isolated large protein powder, mixed vitamin mineral mixture and gamboge extract powder.

Chinese patent application CN201910852672.8 discloses a composition for helping to control body weight and a method for preparing the same, and the composition includes the following components: 400-500 parts of enzymolysis oat flour, 100-300 parts of milk and products thereof, 50-150 parts of vegetable fat powder, 10-30 parts of medium chain triglyceride powder, 10-90 parts of soybean protein, 5-30 parts of fruit and vegetable powder, 35-105 parts of resistant dextrin, 10-100 parts of oat bran powder, 10-100 parts of konjak powder, 5-60 parts of white kidney bean extract, 5-60 parts of collagen peptide, 3-30 parts of fiber extract, 5-50 parts of bamboo shoot fiber, 5-15 parts of trehalose, 5-50 parts of rice protein and 2-20 parts of vitamins and minerals. The composition prepared by this method has comprehensive nutrition and better weight loss effect, and effectively controls body weight.

The weight loss health food is not a medicine, has few side effects and has great advantages in assisting the control of body weight. At present, composition products with clear effects and effective weight control are still insufficient and cannot meet public demand.

SUMMARY

In view of the above, the disclosure aims to provide a composition for weight reduction and body fat reduction and its preparation method and application, which has the effects of blocking fat absorption, accelerating fat metabolism and keeping satiety feeling, and has multiple functions and effects of reducing weight, reducing blood sugar and reducing body fat.

In order to achieve the above purpose, the technical scheme of the disclosure is as follows:

In one aspect, the disclosure provides a composition for weight reduction and body fat reduction, which includes the following components in parts by weight:

10-30 parts of concentrated milk protein, 10-30 parts of soybean isolated protein powder, 10-30 parts of concentrated whey protein powder, 5-15 parts of skim milk powder, 0.5-15 parts of collagen peptide, 0.1-3 parts of *Agaricus bisporus* extract, 0.1-3 parts of *Flammulina velutipes* extract, 0.1-5 parts of okra powder, 0.1-2 parts of *Opuntia ficus-indica* extract, 1-10 parts of medium chain triglyceride microcapsule powder, 0.1-5 parts of mango concentrated powder, 0.1-2 parts of ginger oil microcapsule powder, 0.1-2 parts of citrus powder, 0.1-5 parts of guarana extract and 0.5-2 parts of compound vitamin.

Preferably, the weight ratio of the concentrated milk protein, the soybean isolated protein powder, the concentrated whey protein powder, the skim milk powder and the collagen peptide is 15-25:15-25:15-25:8-12:3-12, and even more preferably 20:20:20:12:8.

Preferably, the weight ratio of the *Agaricus bisporus* extract, the *Flammulina velutipes* extract, the okra powder and the *Opuntia ficus-indica* extract is 1-2:1-2:1-4:0.5-1.5, and even more preferably 1:1:3:1.

Preferably, the weight ratio of the medium chain triglyceride microcapsule powder, the mango concentrated powder, the ginger oil microcapsule powder, the citrus powder and the guarana extract is 2-8:1-4:0.5-1.5:0.5-1.5:1-3, and even more preferably 5:3:1:1:2.

Preferably, the composition for weight reduction and body fat reduction includes the following components in parts by weight: 15-25 parts of concentrated milk protein, 15-25 parts of soybean isolated protein powder, 15-25 parts of concentrated whey protein powder, 8-12 parts of skim milk powder, 3-12 parts of collagen peptide, 1-2 parts of *Agaricus bisporus* extract, 1-2 parts of *Flammulina velutipes* extract, 1-4 parts of okra powder, 0.5-1.5 parts of *Opuntia ficus-indica* extract, 2-8 parts of medium chain triglyceride microcapsule powder, 1-4 parts of mango concentrated powder, 0.5-1.5 parts of ginger oil microcapsule powder, 0.5-1.5 parts of citrus powder, 1-3 parts of guarana extract and 1-2 parts of compound vitamin.

Further preferably, the composition for weight reduction and body fat reduction includes the following components in parts by weight: 20 parts of concentrated milk protein, 20 parts of soybean isolated protein powder, 20 parts of concentrated whey protein powder, 12 parts of skim milk powder, 8 parts of collagen peptide, 1 part of *Agaricus bisporus* extract, 1 part of *Flammulina velutipes* extract, 3 parts of okra powder, 1 part of *Opuntia ficus-indica* extract, 5 parts of medium chain triglyceride microcapsule powder, 3 parts of mango concentrated powder, 1 part of ginger oil microcapsule powder, 1 part of citrus powder, 2 parts of guarana extract and 2 parts of compound vitamin.

The compound vitamin includes vitamin A, vitamin B1, vitamin B2, vitamin B6, vitamin C and vitamin E.

As a specific embodiment of the present disclosure, in the compound vitamin, the weight ratio of vitamin A, vitamin B1, vitamin B2, vitamin B6, vitamin C and vitamin E is 1:3:1:1:100:10.

Preferably, the composition for weight control for overweight people can further includes common auxiliary materials in food.

The auxiliary materials are selected from at least one of sweetener, sour agent, stabilizer, thickener, natural food pigment and food essence.

In another aspect, the present disclosure provides a method for preparing the above composition for weight reduction and body fat reduction, including the steps of:
(1) mixing medium chain triglyceride microcapsule powder, mango concentrated powder, ginger oil microcapsule powder, citrus powder and guarana extract with the formulation dosage, adding water, and uniformly mixing to obtain a compound 1;
(2) adding *Agaricus bisporus* extract, *Flammulina velutipes* extract, okra powder and *Opuntia ficus-indica* extract with the formulation dosage into the compound obtained in the step (1), and uniformly mixing to obtain a compound 2;
(3) drying the compound 2 obtained in the step (2) to obtain a dried material;
(4) mixing the dried material with concentrated milk protein, soybean isolated protein powder, concentrated whey protein powder, skim milk powder, collagen peptide and compound vitamin with the formulation dosage to obtain the composition for weight control for overweight people.

Preferably, in step (1), the solids content of the compound 1 is 30% to 70%, preferably 45%.

Preferably, in step (3), the drying means is preferably spray drying.

Finally, the disclosure provides applications of the composition for weight reduction and body fat reduction in health products and dietary supplements.

The beneficial effects of the disclosure are as follows:

The addition of the concentrated milk protein powder, the soybean isolated protein powder, the concentrated whey protein powder, the skim milk powder and the collagen peptide in the present disclosure can provide long-lasting satiety feeling and supplement protein. The compounding of the *Agaricus bisporus* extract, the *Flammulina velutipes* extract, the okra powder and the *Opuntia ficus-indica* extract has the effect of blocking fat absorption and promoting fat metabolism. The compounding of the medium chain triglyceride microcapsule powder, the mango concentrated powder, the ginger oil microcapsule powder, the citrus powder and the guarana extract further accelerates fat metabolism and achieves good weight loss effects. Meanwhile, multiple compound vitamin is added to the formulation in the present disclosure to enhance its nutritional value.

DETAILED DESCRIPTION OF THE EMBODIMENTS

The following non-limiting embodiments may allow one of ordinary skill in the art to more fully understand the disclosure without limiting the disclosure in any way. The following content is only exemplary description of the scope of protection of the present disclosure, and those skilled in the art can make various changes and modifications to the present disclosure according to the disclosed content, which should also belong to the scope of protection of the present disclosure as claimed.

The disclosure is further illustrated by means of the following specific embodiments. The various chemical reagents used in the embodiments of the present disclosure were obtained by conventional commercial means unless otherwise specified. Unless otherwise specified, the contents are mass contents in the following. Unless otherwise indicated, it is understood that it was carried out at room temperature.

In the following embodiments, the compound vitamin was a composition of vitamin A, vitamin B1, vitamin B2, vitamin B6, vitamin C and vitamin E in a weight ratio of 1:3:1:1:100:10.

In the following embodiments, some raw material purchase information is as follows, but the present disclosure is not limited thereto:

| Raw material | Manufacturer | Article No. |
| --- | --- | --- |
| Concentrated milk protein | Fonterra | 470 |
| Soybean isolated protein powder | Shandong Yuxin Biotechnology Co., Ltd | 787 |
| Concentrated whey protein powder | Shanghai Proqin International Trade Co., Ltd | PROTARMOR 80 |
| Skim milk powder | Hangzhou Juneng Food Co., Ltd | / |
| Collagen Peptide | Jialida (Liaoyuan) Gelatin Co., Ltd | Verisol B (CN) |
| *Agaricus bisporus* extract | Shanghai Ruixinda Health Technology Co., Ltd | / |
| *Flammulina velutipes* extract | Beijing Xinda Qichuang Health Technology Co., Ltd | / |
| Okra powder | Shanghai Yipan Biotechnology Co., Ltd | / |
| *Opuntia ficus-indica* extract | Tianjin Binhai Jiecheng Specialty Chemical Co., Ltd | / |
| Medium chain triglyceride microcapsule powder | Dalian Yinuo Biotechnology Co., Ltd | / |
| Mango concentrated powder | Tianjin Binhai Jiecheng Specialty Chemical Co., Ltd | / |
| Ginger oil microcapsule powder | Xi'an Nuozhong Kangjian Biotechnology Co., Ltd | 10% Gingerol |
| Citrus powder | Guangzhou Mile Biotechnology Co., Ltd | / |

| Raw material | Manufacturer | Article No. |
|---|---|---|
| Guarana Extract | Hangzhou Tiancao Technology Co., Ltd | 10% |

Embodiments 1-7, comparative examples 1-6 were formulated as follows:

Embodiment 1

20 parts of concentrated milk protein, 20 parts of soybean isolated protein powder, 20 parts of concentrated whey protein powder, 12 parts of skim milk powder, 8 parts of collagen peptide, 1 part of *Agaricus bisporus* extract, 1 part of *Flammulina velutipes* extract, 3 parts of okra powder, 1 part of *Opuntia ficus-indica* extract, 5 parts of medium chain triglyceride microcapsule powder, 3 parts of mango concentrated powder, 1 part of ginger oil microcapsule powder, 1 part of citrus powder, 2 parts of guarana extract and 2 parts of compound vitamin.

Embodiment 2

15 parts of concentrated milk protein, 25 parts of soybean isolated protein powder, 15 parts of concentrated whey protein powder, 12 parts of skim milk powder, 3 parts of collagen peptide, 2 parts of *Agaricus bisporus* extract, 1 part of *Flammulina velutipes* extract, 4 parts of okra powder, 0.5 parts of *Opuntia ficus-indica* extract, 8 parts of medium chain triglyceride microcapsule powder, 1 part of mango concentrated powder, 1.5 parts of ginger oil microcapsule powder, 0.5 parts of citrus powder, 3 parts of guarana extract and 1 part of compound vitamin.

Embodiment 3

25 parts of concentrated milk protein, 15 parts of soybean isolated protein powder, 25 parts of concentrated whey protein powder, 8 parts of skim milk powder, 12 parts of collagen peptide, 1 part of *Agaricus bisporus* extract, 2 parts of *Flammulina velutipes* extract, 1 part of okra powder, 1.5 parts of *Opuntia ficus-indica* extract, 2 parts of medium chain triglyceride microcapsule powder, 4 parts of mango concentrated powder, 0.5 parts of ginger oil microcapsule powder, 1.5 parts of citrus powder, 1 part of guarana extract and 2 parts of compound vitamin.

Embodiment 4

10 parts of concentrated milk protein, 30 parts of soybean isolated protein powder, 10 parts of concentrated whey protein powder, 15 parts of skim milk powder, 0.5 parts of collagen peptide, 1 part of *Agaricus bisporus* extract, 1 part of *Flammulina velutipes* extract, 3 parts of okra powder, 1 part of *Opuntia ficus-indica* extract, 10 parts of medium chain triglyceride microcapsule powder, 0.5 parts of mango concentrated powder, 2 parts of ginger oil microcapsule powder, 0.1 parts of citrus powder, 5 parts of guarana extract and 0.5 parts of compound vitamin.

Embodiment 5

10 parts of concentrated milk protein, 30 parts of soybean isolated protein powder, 10 parts of concentrated whey protein powder, 15 parts of skim milk powder, 0.5 parts of collagen peptide, 3 parts of *Agaricus bisporus* extract, 0.5 parts of *Flammulina velutipes* extract, 5 parts of okra powder, 0.1 parts of *Opuntia ficus-indica* extract, 5 parts of medium chain triglyceride microcapsule powder, 3 parts of mango concentrated powder, 1 part of ginger oil microcapsule powder, 1 part of citrus powder, 2 parts of guarana extract and 0.5 parts of compound vitamin.

Embodiment 6

10 parts of concentrated milk protein, 30 parts of soybean isolated protein powder, 10 parts of concentrated whey protein powder, 15 parts of skim milk powder, 0.5 parts of collagen peptide, 3 parts of *Agaricus bisporus* extract, 0.5 parts of *Flammulina velutipes* extract, 5 parts of okra powder, 0.1 parts of *Opuntia ficus-indica* extract, 10 parts of medium chain triglyceride microcapsule powder, 0.5 parts of mango concentrated powder, 2 parts of ginger oil microcapsule powder, 0.1 parts of citrus powder, 5 parts of guarana extract and 0.5 parts of compound vitamin.

Embodiment 7

30 parts of concentrated milk protein, 10 parts of soybean isolated protein powder, 30 parts of concentrated whey protein powder, 5 parts of skim milk powder, 15 parts of collagen peptide, 0.5 parts of *Agaricus bisporus* extract, 3 parts of *Flammulina velutipes* extract, 0.5 parts of okra powder, 2 parts of *Opuntia ficus-indica* extract, 1 part of medium chain triglyceride microcapsule powder, 5 parts of mango concentrated powder, 0.1 parts of ginger oil microcapsule powder, 2 parts of citrus powder, 0.5 parts of guarana extract and 2 parts of compound vitamin.

Comparative Example 1

The difference from embodiment 1 is that in the formulation of comparative example 1, no *Agaricus bisporus* extract was added, and the *Flammulina velutipes* extract was added in 2 parts, and the rest were the same.

Comparative Example 2

The difference from embodiment 1 is that in the formulation of comparative example 2, no *Opuntia ficus-indica* extract was added, and the *Flammulina velutipes* extract was added in 2 parts, and the rest were the same.

Comparative Example 3

The difference from embodiment 1 is that in the formulation of comparative example 3, no ginger oil microcapsule powder was added, and the medium chain triglyceride microcapsule powder was added in 6 parts, and the rest were the same.

Comparative Example 4

The difference from embodiment 1 is that the mango concentrated powder was replaced by the conjugated linoleic acid microcapsule powder in the same amount, and the rest were the same.

Comparative Example 5

20 parts of concentrated milk protein, 20 parts of soybean isolated protein powder, 20 parts of concentrated whey protein powder, 12 parts of skim milk powder, 8 parts of collagen peptide, 4 parts of *Agaricus bisporus* extract, 4 parts of *Flammulina velutipes* extract, 0.3 parts of okra powder, 3 parts of *Opuntia ficus-indica* extract, 5 parts of medium chain triglyceride microcapsule powder, 3 parts of mango concentrated powder, 1 part of ginger oil microcapsule powder, 1 part of citrus powder, 2 parts of guarana extract and 2 parts of compound vitamin.

Comparative Example 6

20 parts of concentrated milk protein, 20 parts of soybean isolated protein powder, 20 parts of concentrated whey protein powder, 12 parts of skim milk powder, 8 parts of collagen peptide, 1 part of *Agaricus bisporus* extract, 1 part of *Flammulina velutipes* extract, 3 parts of okra powder, 1 part of *Opuntia ficus-indica* extract, 12 parts of medium chain triglyceride microcapsule powder, 0.1 parts of mango concentrated powder, 3 parts of ginger oil microcapsule powder, 0.5 parts of citrus powder, 1 part of guarana extract and 2 parts of compound vitamin.

Preparation Example

Compositions of all embodiments and comparative examples were prepared according to the following method, in their respective formulations:
(1) mixing medium chain triglyceride microcapsule powder, mango concentrated powder, ginger oil microcapsule powder, citrus powder and guarana extract with the formulation dosage, adding purified water, adjusting the solid content to 45%, stirring, and fully and uniformly mixing to obtain a compound 1;
(2) adding *Agaricus bisporus* extract, *Flammulina velutipes* extract, okra powder and *Opuntia ficus-indica* extract with the formulation dosage into the compound obtained in the step (1), stirring, and fully and uniformly mixing to obtain a compound 2;
(3) spray drying the compound 2 obtained in the step (2) to obtain a dried material;
(4) fully mixing the dried material with concentrated milk protein, soybean isolated protein powder, concentrated whey protein powder, skim milk powder, collagen peptide and compound vitamin with the formulation dosage to obtain the composition for weight reduction and body fat reduction.

Result Detection

1. Animal Experiment

Experimental animals: male C57BL/6 mice, 4 weeks old;

Feeding conditions: mice were housed in plastic cages, with a 12/12 h light/dark cycle, free access to water and diet (tap water for drinking water, basic feed including corn, wheat, alfalfa, fish meal, soybean meal, chicken meal, vegetable oil, amino acids, vitamins, minerals, etc.), at temperature of 25° C. and air humidity of 40-60%, in a stable environment, with adaptive feeding.

Grouping: after one week of adaptive feeding, the mice were randomly divided into 15 groups with 10 mice in each group, wherein 13 groups were experimental groups and the compositions of embodiments 1 to 7 and comparative examples 1 to 6 were respectively given, one group was a model group and one group was a blank group.

Feeding mode: the blank group was continuously fed with the original basic feed, the model group and the experimental groups were fed with the high-fat feed (made by uniformly mixing the original basic feed, lard and egg yolk powder in a mass ratio of 7:2:1), the feeding amount was 80 g/kg (mouse weight), and the mice could drink water and move freely.

During the experiment, the experimental groups were given aqueous solutions of the compositions prepared in embodiments 1 to 7 and comparative examples 1 to 6 by gavage, respectively, where the amount of the composition was 500 mg/kg (mouse weight), and the normal group and the model group were given equal amounts of physiological saline by gavage at a volume of 10 mL/kg, and the gavage continued for 4 weeks. The initial weight average value M0 before the gavage of each group of mice and the weight average value M1 at the fourth week after the gavage were recorded, and the body fat was weighed by laparotomy after the experiment was completed.

The weights of the mice were weighed as follows:

| Group | M0 (g) | M1 (g) |
|---|---|---|
| Blank group | 16.13 ± 0.14 | 22.64 ± 1.67ΔΔ |
| Model group | 16.48 ± 0.27 | 35.19 ± 2.57**## |
| Embodiment 1 group | 16.34 ± 0.16 | 22.84 ± 1.06ΔΔ |
| Embodiment 2 group | 15.86 ± 0.15 | 24.21 ± 1.03ΔΔ |
| Embodiment 3 group | 15.90 ± 0.18 | 23.90 ± 0.96ΔΔ |
| Embodiment 4 group | 16.27 ± 0.09 | 24.73 ± 1.47ΔΔ |
| Embodiment 5 group | 15.94 ± 0.11 | 24.55 ± 2.12ΔΔ |
| Embodiment 6 group | 16.07 ± 0.14 | 24.62 ± 1.68ΔΔ |
| Embodiment 7 group | 16.22 ± 0.20 | 25.34 ± 2.04ΔΔ*# |
| Comparative example 1 group | 16.31 ± 0.24 | 31.38 ± 2.37**## |
| Comparative example 2 group | 15.91 ± 0.13 | 32.07 ± 1.95**## |
| Comparative example 3 group | 16.16 ± 0.19 | 30.22 ± 2.37**## |
| Comparative example 4 group | 16.36 ± 0.18 | 28.85 ± 1.62*Δ# |
| Comparative example 5 group | 16.09 ± 0.11 | 30.34 ± 2.34**# |
| Comparative example 6 group | 16.20 ± 0.16 | 30.61 ± 1.88**# |

Note:
compared with the blank group, *$P < 0.05$, **$P < 0.01$; compared with the model group, Δ$P < 0.05$, ΔΔ$P < 0.01$; compared with the embodiment 1 group, #$P < 0.05$, ##$P < 0.01$.

Body fat weighing results were as follows:

| Group | Total body fat weight (g) |
|---|---|
| Blank group | 2.87 ± 0.14ΔΔ |
| Model group | 5.26 ± 0.65**## |
| Embodiment 1 group | 2.76 ± 0.31ΔΔ |
| Embodiment 2 group | 2.91 ± 0.28ΔΔ |
| Embodiment 3 group | 2.85 ± 0.36ΔΔ |
| Embodiment 4 group | 2.96 ± 0.17ΔΔ |
| Embodiment 5 group | 2.92 ± 0.29ΔΔ |
| Embodiment 6 group | 3.15 ± 0.31*Δ |
| Embodiment 7 group | 3.22 ± 0.17*Δ |
| Comparative example 1 group | 4.59 ± 0.44**## |

-continued

| Group | Total body fat weight (g) |
|---|---|
| Comparative example 2 group | 4.71 ± 0.32**## |
| Comparative example 3 group | 4.05 ± 0.17**Δ# |
| Comparative example 4 group | 3.78 ± 0.34**# |
| Comparative example 5 group | 4.32 ± 0.36**## |
| Comparative example 6 group | 4.13 ± 0.42*# |

Note:
compared with the blank group, *P < 0.05, **P < 0.01; compared with the model group, ΔP < 0.05, ΔΔP < 0.01; compared with embodiment 1 group, #P < 0.05, ##P < 0.01.

From the results in the tables, the formulations of embodiments 1 to 7 significantly inhibited weight gain in mice caused by a high fat diet, and the weight loss effect of embodiment 1 was best from the specific data presentation. Meanwhile, the body fat change result of the mice shows that the composition of the present disclosure has the effects of promoting fat metabolism and reducing the content of fat in the body.

The results of comparative examples 1 to 3 show that the weight reduction effect is poor without the addition of *Agaricus bisporus* extract, *Opuntia ficus-indica* extract or ginger oil microcapsule powder, indicating the interaction between the ingredients in the formulation, which further improves the weight reduction effect. In comparative example 4, the weight reduction effect of the conjugated linoleic acid microcapsule powder instead of the mango concentrated powder is obviously inferior to that of embodiment 1, which shows that the mango concentrated powder has better performance than the conjugated linoleic acid microcapsule powder in the formulation of the disclosure.

In comparative example 5, the weight reduction effect is obviously poor due to the change of the compounding ratio of the *Agaricus bisporus* extract, the *Flammulina velutipes* extract, the okra powder and the *Opuntia ficus-indica* extract, and in comparative example 6, the weight reduction effect is obviously poor due to the change of the compounding ratio of the medium chain triglyceride microcapsule powder, the mango concentrated powder, the ginger oil microcapsule powder, the citrus powder and the guarana extract, which means that the compounding of the *Agaricus bisporus* extract, the *Flammulina velutipes* extract, the okra powder and the *Opuntia ficus-indica* extract in a specific ratio plays the best role in blocking fat absorption and promoting fat metabolism, and the compounding of the medium chain triglyceride microcapsule powder, the mango concentrated powder, the ginger oil microcapsule powder, the citrus powder and the guarana extract in a specific ratio plays the best role in accelerating fat metabolism, which realizes the better weight reduction effect.

2. Volunteer Experiment

Twelve healthy adults, including six men and six women, were selected in each group. The age group was 20-35 years old, and the BMI was 24-32 kg/m². They had no other metabolic diseases, digestive system diseases, endocrine system diseases and mental diseases, etc.; they had no history of allergies or intolerances to the food under test, no recent gastrointestinal diseases or taking any drugs. Subjects were trained prior to the experiment and informed consent was signed.

Control group 1: each subject ate normally according to the recommended daily nutrient intake recommended by the Chinese Nutrition Association, and drank 150 mL of warm water within 30 min before meals, once in the morning and once in the evening.

Experiment group 1: each subject ate normally according to the recommended daily nutrient intake recommended by the Chinese Nutrition Association, and ate 15 g of the composition provided in embodiment 1 (brewed with 150 mL warm water) within 30 min before meals, once in the morning and once in the evening.

Experiment group 2: each subject ate normally according to the recommended daily nutrient intake recommended by the Chinese Nutrition Association, and ate 15 g of the composition provided in comparative example 4 (brewed with 150 mL warm water) within 30 min before meals, once in the morning and once in the evening.

Test instrument: body composition analyzer, Jawon, model ioi353.

The data testing mode was as follows: ① Body weight and body fat: body weight and body fat were measured on the first morning after the start of the experiment and on the next morning after the end of the experiment following empty urine on an empty stomach, ② Satiety feeling: the satiety feeling was fed back 2 hours after breakfast and dinner, and the satiety feeling was recorded in four ways of hunger, general, better and good.

For 30 consecutive days, the body weight, body fat and satiety feeling of each group of subjects were detected and recorded, and the statistical results were as follows:

| Group | Average weight change | Average changes in body fat | Average satiety feeling |
|---|---|---|---|
| Control group 1 | Increase by 0.4 kg | Increase by 0.2 kg | General |
| Experimental Group 1 | Reduce by 2.8 kg | Reduce by 2.4 kg | Better |
| Experimental Group 2 | Reduce by 1.3 kg | Reduce by 1.5 kg | Better |

The results show that for overweight people, most of the them are in a fat-prone constitution, the products used in the experiment group 1 have good weight and body fat reducing effects under the same dietary structure, and the products in the experiment group 2 also have certain weight and fat reducing effects, but the effects are obviously inferior to those of the experiment group 1, so that the composition of the embodiment 1 is optimal.

The foregoing descriptions are merely exemplary embodiments of the present disclosure, but are not intended to limit the present disclosure. Any modification, equivalent replacement, or improvement made within the spirit and principle of the present disclosure shall belong to the scope of protection of the present disclosure.

What is claimed is:

1. A composition for weight reduction and body fat reduction, consisting of following components in parts by weight: 10-30 parts of concentrated milk protein, 10-30 parts of soybean isolated protein powder, 10-30 parts of concentrated whey protein powder, 5-15 parts of skim milk powder, 0.5-15 parts of collagen peptide, 0.5-3 parts of *Agaricus bisporus* extract, 0.5-3 parts of *Flammulina velutipes* extract, 0.5-5 parts of okra powder, 0.1-2 parts of *Opuntia ficus-indica* extract, 1-10 parts of medium chain triglyceride microcapsule powder, 0.5-5 parts of mango concentrated powder, 0.1-2 parts of ginger oil microcapsule powder, 0.1-2 parts of citrus powder, 0.5-5 parts of guarana extract and 0.5-2 parts of compound vitamin;
   a weight ratio of the *Agaricus bisporus* extract, the *Flammulina velutipes* extract, the okra powder and the *Opuntia ficus-indica* extract is 1-2:1-2:1-4:0.5-1.5; a weight ratio of the medium chain triglyceride microcapsule powder, the mango concentrated powder, the ginger oil microcapsule powder, the citrus powder and the guarana extract is 2-8:1-4:0.5-1.5:0.5-1.5:1-3; the compound vitamin comprises vitamin A, vitamin B1, vitamin B6, vitamin B12, vitamin C, vitamin E and vitamin D;
   Ginger oil microcapsule powder contains 10% gingerol.

2. The composition for weight reduction and body fat reduction of claim 1, wherein a weight ratio of the concentrated milk protein, the soybean isolated protein powder, the concentrated whey protein powder, the skim milk powder and the collagen peptide is 15-25:15-25:15-25:8-12:3-12.

3. The composition for weight reduction and body fat reduction of claim 1, wherein a weight ratio of the concentrated milk protein, the soybean isolated protein powder, the concentrated whey protein powder, the skim milk powder and the collagen peptide is 20:20:20:12:8.

4. The composition for weight reduction and body fat reduction of claim 1, wherein a weight ratio of the *Agaricus bisporus* extract, the *Flammulina velutipes* extract, the okra powder and the *Opuntia ficus-indica* extract is 1:1:3:1.

5. The composition for weight reduction and body fat reduction of claim 1, wherein a weight ratio of the medium chain triglyceride microcapsule powder, the mango concentrated powder, the ginger oil microcapsule powder, the citrus powder and the guarana extract is 5:3:1:1:2.

6. The composition for weight reduction and body fat reduction of claim 1, wherein the composition consists of the following components in parts by weight: 15-25 parts of concentrated milk protein, 15-25 parts of soybean isolated protein powder, 15-25 parts of concentrated whey protein powder, 8-12 parts of skim milk powder, 3-12 parts of collagen peptide, 1-2 parts of *Agaricus bisporus* extract, 1-2 parts of *Flammulina velutipes* extract, 1-4 parts of okra powder, 0.5-1.5 parts of *Opuntia ficus-indica* extract, 2-8 parts of medium chain triglyceride microcapsule powder, 1-4 parts of mango concentrated powder, 0.5-1.5 parts of ginger oil microcapsule powder, 0.5-1.5 parts of citrus powder, 1-3 parts of guarana extract and 1-2 parts of compound vitamin.

7. The composition for weight reduction and body fat reduction of claim 6, wherein the composition consists of the following components in parts by weight: 20 parts of concentrated milk protein, 20 parts of soybean isolated protein powder, 20 parts of concentrated whey protein powder, 12 parts of skim milk powder, 8 parts of collagen peptide, 1 part of *Agaricus bisporus* extract, 1 part of *Flammulina velutipes* extract, 3 parts of okra powder, 1 part of *Opuntia ficus-indica* extract, 5 parts of medium chain triglyceride microcapsule powder, 3 parts of mango concentrated powder, 1 part of ginger oil microcapsule powder, 1 part of citrus powder, 2 parts of guarana extract and 2 parts of compound vitamin.

8. A method for preparing the composition for weight reduction and body fat reduction of claim 1, comprising the steps of:
   (1) mixing medium chain triglyceride microcapsule powder, mango concentrated powder, ginger oil microcapsule powder, citrus powder and guarana extract according to the parts by weight of the components, adding water, and uniformly mixing to obtain a compound 1;
   (2) adding *Agaricus bisporus* extract, *Flammulina velutipes* extract, okra powder and *Opuntia ficus-indica* extract according to the parts by weight of the components into the compound obtained in the step (1), and uniformly mixing to obtain a compound 2;
   (3) drying the compound 2 obtained in the step (2) to obtain a dried material;
   (4) mixing the dried material with concentrated milk protein, soybean isolated protein powder, concentrated whey protein powder, skim milk powder, collagen peptide and compound vitamin according to the parts by weight of the components to obtain the composition for weight reduction and body fat reduction.

* * * * *